United States Patent [19]

Nishi et al.

[11] 4,078,202
[45] Mar. 7, 1978

[54] APPARATUS FOR DETECTING WIRE JOINT

[75] Inventors: Satoru Nishi, Kishiwada; Katsumasa Tanaka, Ono, both of Japan

[73] Assignee: Kobe Steel, Ltd., Kobe, Japan

[21] Appl. No.: 698,409

[22] Filed: Jun. 21, 1976

[30] Foreign Application Priority Data

Feb. 25, 1976 Japan .................................. 51-20343

[51] Int. Cl.$^2$ ............................................ G01R 27/26
[52] U.S. Cl. ...................................... 324/61 R; 28/227
[58] Field of Search ...................... 324/61 R, 61 P, 65; 73/104, 105; 28/64

[56] References Cited

U.S. PATENT DOCUMENTS

| 3,421,078 | 1/1969 | Corman | 324/61 |
|---|---|---|---|
| 3,523,246 | 8/1970 | Hall et al. | 324/61 |
| 3,973,187 | 8/1976 | Cereijo et al. | 324/61 R |
| 3,984,767 | 10/1976 | Denton et al. | 324/61 R |

*Primary Examiner*—Stanley T. Krawczewicz
*Assistant Examiner*—Vincent J. Sunderdick
*Attorney, Agent, or Firm*—Oblon, Fisher, Spivak, McClelland & Maier

[57] ABSTRACT

Apparatus in a continuous processing line or wire wherein a welded joint, a disconnected part or an entangled part of a metallic wire, traveling continuously, is detected by sensing a variation in the electrostatic capacity between a detecting element and the wire member. The detecting element is so supported as to be displaceable when pressed by the metallic wire, which passes over an auxiliary roller which is disposed at a position opposite to the detecting element, with the wire moving therebetween. A pair of guide rollers disposed forwardly and rearwardly of the detecting element, in the traveling direction of the wire, and a pair of press rollers are disposed on the same side as that of the detecting element and between the detecting element and the guide rollers in order to normally hold the wire member to be detected in contact with the auxiliary roller.

6 Claims, 5 Drawing Figures

APPARATUS FOR DETECTING WIRE JOINT

BACKGROUND OF THE INVENTION

In a secondary working process of a wire, the wire is subjected to a heat treatment before drawing. Usually, the heat treatment is continuously carried out on the wire in a strand form, from the viewpoint of job efficiency. To this end, the wires to be supplied to a heat treatment furnace are continuous ones which are connected by butt welding or the like. More specifically, as shown in FIG. 1, the terminal end part of a wire (a) and the initial end part of a wire (b) are connected by such a butt welding operation. A welding burr exists at the connected part. Although the welding burr differs variously according to the welding conditons, a wire having a diameter of 1.0 - 15 mm will give rise to a burr whose width, or axial extent, taken in the traveling direction of the wire, is about 3 - 10 mm and whose diameter is about 1.5 - 40 mm. Such welding burrs are cut off and discarded at the point of take-up of the wire after completion of the heat treatment, so that they are not mixed in a coil of the wire so taken up. Accordingly, an operator engaged in the take-up of the wire after it has been subjected to such heat treatment has been responsible for conducting the job of reliably cutting off and discarding the welding burr parts during the take-up of the wire, while continuously observing them. In order to facilitate the detection of the welding burr part, i.e., the connected position of the wire, the welding burr part has hitherto beeen made conspicuous or attractive by winding a fine iron wire or the like round the welding burr part. The use of the fine iron wire or the like is based on the fact that, since the stranded wire passes through the heat treatment furnace at a high temperature, conventional display means, such as coloration, cannot be utilized for the detection of the connected position. The fine iron wire, or the like, is suitable as one which keeps its original form even when heated to the extent of the heat treatment temperature. All the pertinent jobs, however, rely on manpower. In particular, the passage of the wire subjected to the heat treatment need be continually observed in order to detect the connected positions. This has required much labor. Moreover, the detection precision has tended to become lower, especially as the number of wires to be processed and the processing speed thereof is increased.

In order to eliminate the disadvantages thereby encountered, there has recently been proposed a method in which, as disclosed in Japanese Patent Application Public-disclosure No. 2654/1975, the connected wire part is detected by a phototube switch, or the like, having a contactless mechanism. However, this method is not yet completely satisfactory, primarily because the size of the welding burr changes largely in dependence, not only on the wire diameter, but also on the welding conditions, etc. Thus, in the phototube switch having such a contactless mechanism, the adjustment of the light projecting face is a difficult job, particularly in such cases where the welding burr lies at the connected part at a change from a wire of larger diameter to a wire of smaller diameter, whereby the detection precision for the connected part generally lowers. Besides, the phototube switch must be arranged for each individual wire to be detected, so that the method is disadvantageous in cost.

U.S. Pat. No. 3,812,424 has proposed an expedient in which the cross sectional area of a wire is gauged by measuring an electrostatic capacity. Herein, a sensing electrode is formed in a manner to surround one wire. In order to detect defects of a plurality of wires at the same time, therefore, a number of electrodes are required according to the number of the wires. It is accordingly difficult to detect the welded joints of the plurality of wires at a stroke. Further means to detect defective parts by measuring electrostatic capacities are taught in U.S. Pat. Nos. 2,565,500; 3,052,826; 3,519,922; 3,684,089; 3,764,899; 3,827,296 and 3,879,660 and DT-OS's No. 1,918,715; 2,137,545 and 2,025,644. None of them, however, can be said to be an effective and satisfactory technique for detecting a welded joint, an entangled part and/or a disconnected part of a wire in the continuous heat treatment of the wire, and especially where a plurality of wires are being considered at once. Accordingly, the development of a technique for successfully meeting this purpose is desired.

SUMMARY OF THE INVENTION

This invention has a primary objective of eliminating the disadvantages of the prior art devices and providing an improved detecting apparatus which is most suitable for detecting a welded joint, an entangled part and/or a disconnected part of a wire during the continuous heat treatment of the wire.

Another object of this invention is to provide a detecting apparatus of simple structure and high reliability which detects such welded joints, entangled parts and/or disconnected parts of a plurality of metallic wires automatically and at the same time.

A further object of this invention is to provide a detecting apparatus which makes unnecessary the labor having heretofore been required for observing a welded joint, an entangled part and/or a disconnected part of a wire and which achieves a reduction in the running cost as well as the maintenance cost of an equipment line in a wire continuous heat treatment line.

A yet further object of this invention is to provide a detecting apparatus which is low in maintenance expenses and long in life.

A still further object of this invention is to provide a detecting apparatus which, even in the case of abnormalities of a large number of wires traveling in parallel relation, can discern which, if any, of such wires is abnormal.

A first aspect of this invention for accomplishing the above-mentioned or other objects resides in apparatus wherein a variation in the electrostatic capacity between a metallic wire traveling continuously and a detecting element is sensed and an abnormality, such as a welded joint, a disconnected part or an entangled part of the wire, being a member to be detected, is detected, characterized by a detecting element which is so supported as to be displaceable when pressed by the metallic wire, an auxiliary roller which is disposed at a position opposite to the detecting element with the member to be detected intervening therebetween, a pair of guide rollers which are disposed before and behind the detecting element in the traveling direction of the wire, and a pair of press rollers which are disposed on the same side as that of the detecting element and between the detecting element and the guide rollers in order to normally hold the member to be detected in contact with the auxiliary roller.

A second aspect of this invention resides in the apparatus of the first aspect characterized in that welded joints, disconnected parts and/or entangled parts of a plurality of metallic wires traveling in parallel paths continuously can be detected by a single detecting element.

A third aspect of this invention resides in the apparatus of the first aspect characterized in that the welded joint and/or entangled part of the metallic wire traveling continuously are/is held in direct contact with the detecting element.

A fourth aspect of this invention resides in the apparatus of the first aspect characterized in that the detecting element is a stainless steel pipe which is suspended by a chain.

A fifth aspect of this invention resides in the apparatus of the first aspect characterized in that, in detecting welded joints, disconnected parts and/or entangled parts of a plurality of metallic wires, the plurality of metallic wires are grouped into a plurality of blocks, one detecting element being provided for each of the blocks, whereby the block of the metallic wires having a welded joint, disconnected part and/or entangled part can be detected.

A sixth aspect of this invention resides in the apparatus of the first asepct characterized in that a transformer is interposed between a control circuit for detecting the variation in the electrostatic capacity between the detecting element and the member to be detected and a power input circuit for said control circuit, whereby the control circuit is not damaged even when the detecting element and the welded joint and/or entangled part of the member to be detected come into direct contact.

DETAILED DESCRIPTION OF THE PREFERRED EMBODIMENTS

Figure 1:
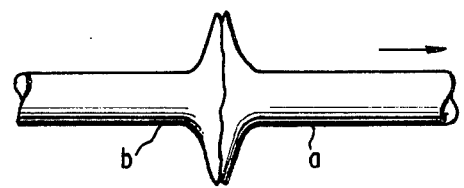
FIG. 1 is a side view showing a welding burr at the connected part of a metallic wire, already described.
Figure 2:
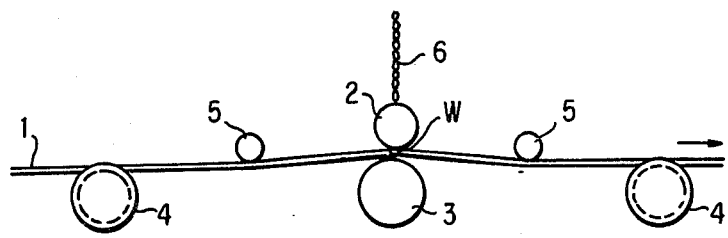
FIG. 2 is a schematic side view of the apparatus of this invention.

Here, the apparatus of this invention will be described in detail with reference to the accompanying drawings, wherein FIG. 2 is a model diagram which shows an embodiment of the apparatus of this invention. A wire 1, which travels in the direction of an arrow, indicated at the right of the figure, passes between a detecting element 2, suspended by a chain 6, and an auxiliary roller 3, which is disposed at a position opposite to the detecting element 2. When a welding burr at the welded joint of the wire 1 passes over the auxiliary roller 3, the wire is pushed up, so that the welded joint can be reliably detected. A grooved guide roller 4 is disposed on both sides of the detecting element 2 and auxiliary roll 3, and between the guide rollers 4 and the detecting element 2 there are disposed press rollers 5, which cause the wire 1 to normally lie in contact with the auxiliary roller 3. When the welded joint W of the wire 1 comes just above the auxiliary roller 3, as illustrated in the figure, it is pushed up by the height of the welding burr and comes into contact with the detecting element 2. Even when contacted by the welding joint W, the detecting element 2 is displaceable, owing to the chain 6. It is not always necessary that the detecting element 2 and the welded joint W of the wire come into direct contact. When the welded joint, entangled part or disconnected part of the wire passes on the auxiliary roller, a variation in the electrostatic capacity between the detecting element 2 and the wire 1 arises. By sensing this variation with a control circuit, to be described later, an abnormal state of the wire can be detected.

Figure 3:
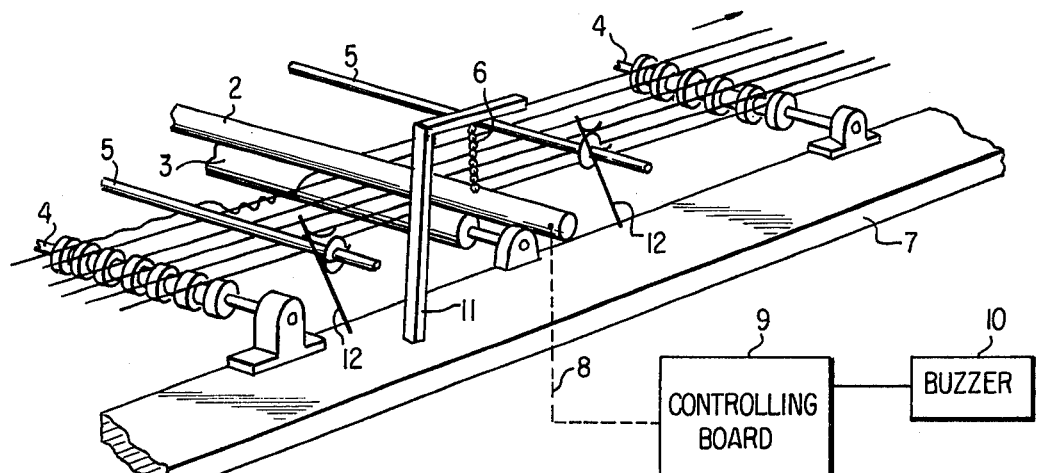
FIG. 3 is a perspective view showing one aspect of performance of the apparatus of this invention.

Referring now to FIG. 3, an embodiment of the apparatus of this invention for detecting abnormalities of a plurality of wires 1 will be explained. The wires 1 which are being taken up in the direction indicated by an arrow at the right of the figure by a winding machine, not shown, pass between an elongate auxiliary roller 3 traversing the wires and the detecting element 2 through grooved guide rollers 4 on which the respective wires travel at predetermined positions and also through the press rollers 5. In this case, a part at which two or more wires are mutually entangled can pass between the detecting element 2 and the auxiliary roller 3 and be taken up via the press roller 5, as well as the guide roller 4. Herein, likewise to the case where the welding joint is detected when the wire passes under the detecting element, the electrostatic capacity between the detecting element and the wires varies. Therefore, the variation is transmitted through a lead wire 8 to a controlling board 9. A buzzer 10 is caused to sound by the control circuit, to be described later, to report that the wires have an abnormality. The guide rollers 4 and the auxiliary roller 3 in the apparatus of this invention are fixed to a base 7, through suitable bearings. The detecting element 2 is suspended by the chain 6 from a frame 11 mounted on the base 7. The press rollers 5 are placed on hooks 12, respectively mounted on the base 7.

Figure 4:
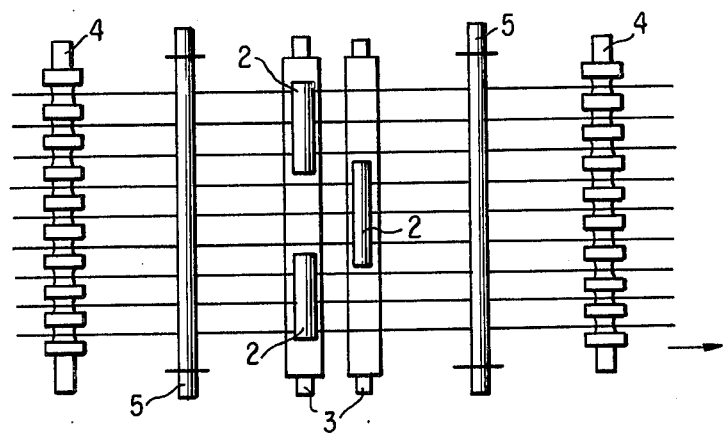
FIG. 4 is a plan view showing another aspect of performance of the apparatus of this invention.

According to this invention, the guide roller 4 is a grooved one for preventing oscillations of the wire 1, particularly those in the horizontal direction, with respect to the traveling of the wire. On the other hand, the press roller 2 functions to enhance the precision of the detection by preventing vertical oscillations of the wire and normally holding the wire 1 in contact with the auxiliary roller 3. The auxiliary roller 3 pushes up the welded joint of the wire 1 towards the detecting element 2, thereby causing the detecting element, situated on the side opposite the auxiliary roller 3, to sense the variation reliably. Besides, in order to prevent the wire from moving excessively toward the detecting element and executing an erroneous operation, even when the wire has a curve, the auxiliary roller 3 is installed about 10 mm higher than the level of the paired guide rollers 4. Employed as the detecting element 2 is a pipe made of stainless steel. While description has been made of the apparatus in which abnormal parts of the plurality of wires traveling in parallel paths are detected by a single detecting element 2, it is also possible to have the abnormal parts detected by a plurality of such detecting elements 2, as illustrated in FIG. 4. In this case, the abnormal parts of every three wires 1, which travel in parallel paths just above two closely positioned parallel auxiliary rollers 3, 3, are detected by three detecting elements 2. It can therefore be easily discerned which of the nine wires is abnormal.

Figure 5:
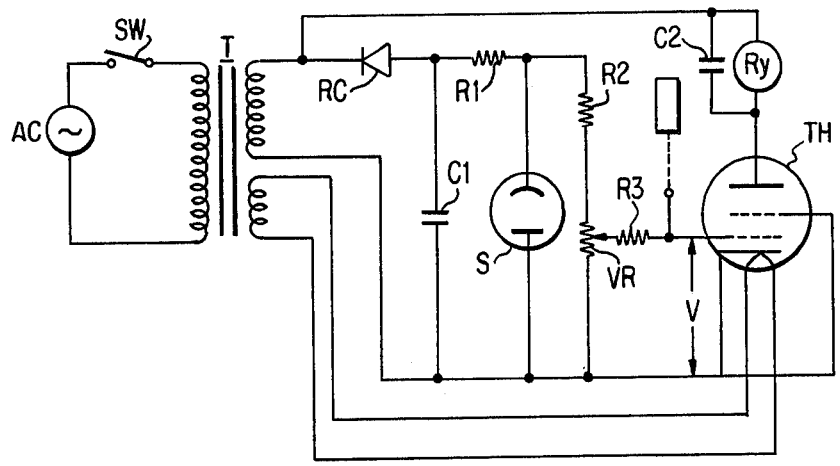
FIG. 5 is a circuit diagram showing a control circuit and a power input circuit of the apparatus of this invention.

The control circuit in the apparatus of this invention will now be explained, with reference being made to FIG. 5. In the figure, AC designates an alternating current source; SW a switch; T a transformer; RC a rectifier; $R_1$, $R_2$ and $R_3$ resistors; $C_1$ and $C_2$ capacitors;

$V_R$ a variable resistor; S a voltage stabilizer; Ry a relay; and TH a thyratron. The detecting element 2 for detecting the abnormal state of the wire 1 is connected through the lead wire 8, shown in FIG. 3, to a grid of the thyratron TH. If the electrostatic capacity varies between the wire 1 and the detecting element 2, the grid voltage V of the thyratron TH will vary. This is, when a welded joint W of the wire has come underneath the detecting element 2, the voltage V increases. Thus, a flow of electrons is induced in the thyratron TH, and the relay Ry is energized to cause the buzzer 10 to sound. When the control circuit is provided with a transformer T between the power source circuit and the control circuit porton, as shown, the control circuit portion is prevented from being damaged even when the abnormal part of the wire comes into contact with the detecting element 2.

By using the apparatus of this invention, as described above, the abnormalities of the wire can be automatically detected, and hence, the manpower previously having to be put into the observing job becomes unnecessary. In addition, the reliability for detecting the abnormalities of the wire has been found to be about 99.9%. Therefore, a detecting apparatus of comparatively simple structure and very high reliability, as provided in this invention, achieves enhancement of the yield of the product, saving of the labor of the operation and convenience of maintenance when used in the secondary working process of the wire.

While the description has been made of the illustrated embodiments for exemplary purposes only, any modifications and variations shall be deemed to fall within the scope of this invention insofar as they are defined in the appended claims.

What is claimed as new and desired to be secured by letters patent of the United States is:

1. An apparatus for detecting a welded joint, a disconnected part and/or entangled part of a metallic wire traveling continuously by detecting a variation in an electrostatic capacity between a detecting element and the wire comprising:
    a. a detecting element supported above said continuously traveling wire so as to be displaceable when pressed upwardly by the metallic wire,
    b. an auxiliary roller disposed at a position opposite to said detecting element with said traveling wire intervening therebetween,
    c. a pair of guide rollers disposed forwardly and rearwardly of said detecting element in a traveling direction of the wire,
    d. a pair of press rollers disposed on the same side of said traveling wire as that of said detecting element and between said detecting element and said guide rollers in order to normally hold said wire in contact with said auxiliary roller, and
    e. means for detecting a variation in the electrostatic capacity between said detecting element and said wire.

2. The apparatus according to claim 1, wherein said pair of guide rollers comprise for guiding a plurality of metallic wires traveling in parallel relation, and said plurality of wires are all detected by the single detecting element.

3. The apparatus according to claim 1, wherein said welded joint and/or entangled part of said metallic wire traveling continuously is held in direct contact with said detecting element.

4. The apparatus according to claim 1, wherein said detecting element is made of stainless steel pipe suspended by a chain.

5. The apparatus according to claim 1, wherein said pair of guide rollers comprise means for guiding a plurality of metallic wires traveling in parallel relation, and a plurality of detecting elements are provided, each of said detecting elements being disposed for a block of said plurality of metallic wires, whereby any of said blocks of said metallic wires having a welded joint, disconnected part and/or entangled part is made detectable.

6. The apparatus according to claim 1, wherein said detecting means comprises a control circuit for detecting the variation in the electrostatic capacity between said detecting element and said wire and a power input circuit for said control circuit, and a transformer is interposed therebetween, whereby said control circuit is not damaged even when said detecting element and the welded joint and/or entangled part of said wire come into direct contact.

* * * * *